United States Patent [19]

Teisseire

[11] 4,146,740
[45] Mar. 27, 1979

[54] INTERMEDIATES USEFUL IN THE PRODUCTION OF NORPATCHOULENOL

[75] Inventor: Paul J. Teisseire, Grasse, France

[73] Assignee: Societe Anonyme Roure Bertrand Dupont, Argenteuil, France

[21] Appl. No.: 767,462

[22] Filed: Feb. 10, 1977

Related U.S. Application Data

[63] Continuation-in-part of Ser. No. 594,335, Jul. 9, 1975, Pat. No. 4,055,594.

[30] Foreign Application Priority Data

Aug. 2, 1974 [CH] Switzerland .................. 10676/74
Apr. 9, 1975 [CH] Switzerland .................. 4602/75

[51] Int. Cl.² ................ C07C 35/22; C07C 35/36
[52] U.S. Cl. .................... 568/817; 195/51 R; 260/598; 560/107; 560/117; 560/249; 560/256; 562/499; 568/665; 568/660
[58] Field of Search ............. 560/256, 249; 260/617 F; 568/817

[56] References Cited

U.S. PATENT DOCUMENTS 3,895,068  7/1975  Duling ..................... 260/617 R
3,925,486  12/1975 Greuter et al. ............. 260/618 R Primary Examiner—Vivian Garner
Attorney, Agent, or Firm—Wallenstein, Spangenberg, Hattis & Strampel

[57] ABSTRACT

Intermediates useful for the synthesis of the valuable perfume material norpatchoulenol, said intermediates having the formula, for instance

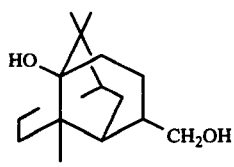
(I)

This intermediate, which is a novel compound, is useful as an intermediate for the production of ethers, esters and other intermediates, which are also novel compounds, such as, for instance, methyl, ethyl, isopropyl and benzyl ethers which can be represented by the formulae

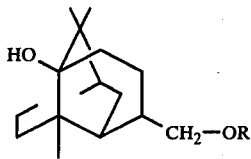
(II)

wherein R is hydrogen or lower carboxylic acyl.

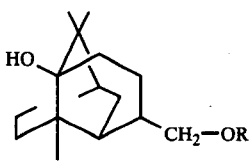

(IIa)

where R is lower alkyl, such as methyl, ethyl, propyl, isopropyl, butyl, isobutyl, benzyl, etc., and

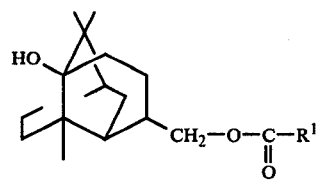
(III)

where

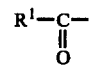

is a lower acyl radical such as acetyl, propionyl, butyryl, benzoyl, etc. Such intermediates are readily prepared by etherification and esterification reaction procedures and said intermediates are useful as intermediates for the preparation of other odorants.

The intermediate of the above formula I is, however, especially valuable for the production of the novel acid-alcohol compound corresponding to the formula

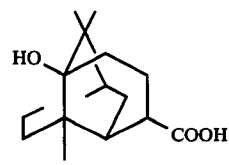
(IV)

which it has been discovered is highly effectively converted, by oxidative decarboxylation, to the valuable perfume material norpatchoulenol which latter has the formula

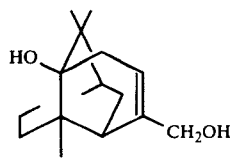
(V)

1 Claim, No Drawings

INTERMEDIATES USEFUL IN THE PRODUCTION OF NORPATCHOULENOL

This is a continuation-in-part of application Ser. No. 594,335, filed July 9, 1975, now U.S. Pat. No. 4,055,594.

DISCUSSION OF THE PRIOR ART

Norpatchoulenol is a known compound described, for example, in French Patent published under the No. 2152522 (filed Sept. 1, 1971). Norpatchoulenol is an extremely important odorant compound which is present in the naturally occurring Patchouli Oil. It only occurs therein at a concentration which is considerably less than that of patchoulol which latter although it is the principal constituent of Patchouli Oil is practically inodorous. The ratio of the concentrations of the two alcohols in Patchouli Oil is of the order of 1:100.

Synthetic methods for the production of norpatchoulenol and key intermediates for its production are disclosed and claimed in the German Patent Applications published under the Nos. 2407782 and 2407781.

OBJECT OF THE PRESENT INVENTION

It is an object of the present invention to provide additional advantageous routes to norpatchoulenol and, more specifically, to provide a certain intermediate which is highly useful for the production of norpatchoulenol, which intermediate is represented by the above formula I.

DETAILED DESCRIPTION OF THE INVENTION

The aforesaid intermediate of formula I is desirably prepared by oxidation of the methyl group in position 4 of patchoulol which has the formula

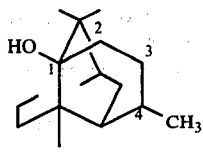

(VI)

whereby to produce the acid alcohol-compound.

This oxidation may be effected by any convenient method, e.g. either by purely chemical means or by a biological process. One particularly interesting biological method for oxidising patchoulol consists of administering patchoulol orally either to rabbits, dogs or rats, which metabolise patchoulol in a practically quantitative yield into a mixture of the acid-alcohol of formula IV and the glycol of formula I.

Another process for the preparation of the acid-alcohol of formula IV utilises the hydroxy-aldehyde of formula

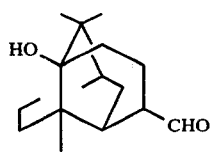

(VII)

The latter can be prepared by careful oxidation of the glycol of formula I, for example by the use of chromic acid in pyridine. The oxidation of the hydroxy-aldehyde of formula VII to the acid-alcohol of formula IV can be effected by any convenient method for example by moist silver oxide (formed in situ from a solution of silver nitrate and ammonium hydroxide).

A certain minor proportion of the hydroxy-aldehyde of formula VII is also formed during the above mentioned biological oxidation of patchoulol in rabbits, dogs or rats.

The invention will now be illustrated with reference to the following Examples.

EXAMPLE 1

The glycol of formula I, together with the acid-alcohol of formula IV, are prepared as follows:

36 hours before administration of the patchoulol, rabbits are put into the metabolism cages. They are left to fast for 24 hours before force feeding. Each rabbit (albino, about 3 kg) receives 1 g (or 1.5 g or 2 g according to trial) of patchoulol in suspension in 20 ml of 1% carboxymethylcellulose solution, then 25 ml of water. These liquid administrations are made by gastric force feeding of the rabbit anaesthetised with Nembutal (about 30 mg/kg). After the force feeding, the rabbits were allowed to partake freely of water and food. All urine passed was collected every 24 hours.

The urine collected over a period of 96 hours is acidified to pH = 4.5 with a solution of 10% HCl. There are added thereto 6 ml of ($\beta$ D-glucuronide)glucuronidase (Suc d'Helix Pomatia de l'Industrie Biologique francaise). The solution is left at 37° for 24 hours, then acidified to pH = 1. After saturating the solution with NaCl, it is extracted with ethyl ether.

Evaporation of the ethyl ether yields a viscous liquid, which is immediately chromatographed on $SiO_2$. There are obtained 10 to 30% of the glycol of formula I, and 20 to 40% of the acid-alcohol of formula IV, with 50% ethyl ether, 50% petroleum ether as eluant.

Glycol of formula I

M.P. = 104°–105° C. $(\alpha)_D^{CHCl_3}$ = −120°
I.R. $\nu_{OH}$ = 3620 and 3450 cm$^{-1}$
N.M.R.

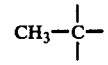

0.85 ppm (s, 3H) and 1.1 ppm (s, 6H)

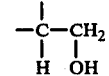

3.45 ppm (d, J=7.5 Hz, 2H)

Monoacetate of the glycol of formula I

I.R. $\nu_{OH}$ = 3600 and 3500 cm$^{-1}$, $\nu_{C=O}$ 1725 cm$^{-1}$
N.M.R.

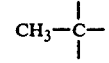

0.85 ppm (s, 3H) and 1.1 ppm (s, 6H)

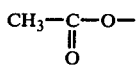

2.05 ppm (s, 3H),

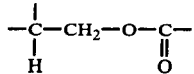

3.90 ppm (d, J=7.5 Hz, 2H).

Acid-alcohol of formula IV

I.R. $\nu_{C=O}$ 1700 cm$^{-1}$
N.M.R.

0.9 ppm (s, 3H) and 1.1 ppm (s, 6H)

Methyl ester of the acid-alcohol of formula IV

I.R. $\nu_{OH}$ = 3600 and 3500 cm$^{-1}$. $\nu_{C=O}$ 1725 cm$^{-1}$
N.M.R.

0.9 ppm (s, 3H), 1.10 ppm (s, 3H) and 1.13 ppm (s, 3H),

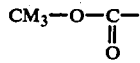

3.65 ppm (s, 3H)

EXAMPLE 2

3 g of a chromic anhydride-pyridine complex are dissolved in 50 ml of methylene chloride to which six drops of pyridine have been added. A solution of 460 mg of the glycol of formula I dissolved in 10 ml of methylene chloride is then added and the reaction mixture is agitated for four hours at the ambient temperature. The reaction mixture is then filtered and the precipitate is washed with 50 ml of methylene chloride. The combined filtrates are then washed successively four times with 10 ml of 5% aqueous sodium hydroxide, three times with 10 ml of 10% aqueous hydrochloric acid, twice with 10 ml of saturated aqueous sodium bicarbonate and finally twice with 10 ml of water. The organic solution is then dried over sodium sulfate and filtered. The solvent is distilled off. There is obtained 465 mg of the hydroxyaldehyde of formula VII which is purified on a silica column. The pure hydroxy-aldehyde has the following characteristics:

$[\alpha_D]^{CHCl_3}$ = $-40°$;

IR; $\nu_{OH}$ at 3500 cm$^{-1}$, $\nu_{C=O}$ at 1715 cm$^{-1}$;
NMR:

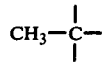

singlet (3H) at 0.89 ppm;

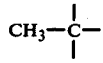

2 singlets coinciding (6H) at 1.08 ppm;

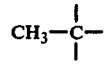

CHO singlet (1H) at 9.64 ppm.

EXAMPLE 3

To a solution of 440 mg of silver nitrate in 1 ml of water there is added, with stirring, a solution of 200 mg of sodium hydroxide in 1 ml of water, then a solution of 146 mg of the hydroxy-aldehyde of formula VII in 0.5 ml of pentane. Stirring is continued at ambient temperature for 30 minutes and the mixture is then heated to 40° C. for two hours. After cooling the mixture is filtered and the precipitate is washed with 10 ml of hot water. The combined filtrates are extracted twice with 5 ml of ethyl ether and then acidified with aqueous 36% w/w hydrochloric acid. Sodium chloride is then added until a saturated solution is obtained. The solution is then extracted three times with 10 ml of diethyl ether. The combined ethereal phases are washed with saturated aqueous sodium chloride and then dried over sodium sulfate. One obtains 110 mg of the acid-alcohol of formula IV having the following physical characteristics:

$[\alpha_D]^{CHCl_3}$ = $-87°$;

IR: $\nu_{CO}$ at 1700 cm$^{-1}$, $\nu_{OH}$ at 3180 and 2600cm$^{-1}$, $\nu_{OH}$ at 3480 cm$^{-1}$; NMR:

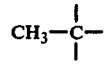

singlet (3H) at 0.88 ppm;

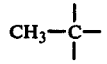

singlet (3H) at 1.08 ppm;

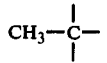

singlet (3H) at 1.11 ppm.

EXAMPLE 4

To a solution of 500 mg of the acid-alcohol of formula IV, 200 mg of cupric acetate and 1 ml of pyridine in 50 ml of benzene, there are added 800 mg of lead tetraacetate. The mixture is then heated under reflux for 30 minutes. After cooling, 1,2-propanediol is added and the mixture is extracted with ethyl ether. Evaporation of the solvent yields an oil which is chromatographed on SiO$_2$; there are thus obtained 300 mg of a product which by comparison of thin layer chromatograms, I.R. and NMR spectra and melting points was shown to be identical to natural norpatchoulenol.

What is claimed is:

1. A compound of the formula

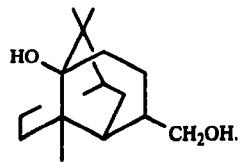

(I)

* * * * *